(12) United States Patent
Gonzalez et al.

(10) Patent No.: US 10,492,801 B2
(45) Date of Patent: Dec. 3, 2019

(54) POWER DRIVEN SURGICAL TOOL

(71) Applicant: OsteoMed LLC, Addison, TX (US)

(72) Inventors: Mario Gonzalez, Addison, TX (US);
Eric Mickelson, Addison, TX (US);
Dan Davison, Addison, TX (US);
Gregg Prisco, Addison, TX (US);
Jason Barber, Addison, TX (US);
Charles R. Forton, Frisco, TX (US);
Brian R. Conroy, Addison, TX (US)

(*) Notice: Subject to any disclaimer, the term of this patent is extended or adjusted under 35 U.S.C. 154(b) by 255 days.

(21) Appl. No.: 15/270,875

(22) Filed: Sep. 20, 2016

(65) Prior Publication Data
US 2018/0078298 A1 Mar. 22, 2018

(51) Int. Cl.
*A61B 17/16* (2006.01)
*A61B 17/00* (2006.01)
*A61B 90/00* (2016.01)

(52) U.S. Cl.
CPC .......... *A61B 17/1622* (2013.01); *A61B 2017/00424* (2013.01); *A61B 2017/00734* (2013.01); *A61B 2090/066* (2016.02)

(58) Field of Classification Search
CPC ..... A61B 17/88; A61B 17/8875; A61B 17/16; A61B 2017/00424; B23B 45/001
See application file for complete search history.

(56) References Cited

U.S. PATENT DOCUMENTS

| | | | |
|---|---|---|---|
| 2,979,089 A * | 4/1961 | Piesker | B25B 21/00 15/23 |
| 4,878,404 A * | 11/1989 | Liao | B25B 21/00 81/54 |
| 5,536,267 A * | 7/1996 | Edwards | A61B 18/1477 604/22 |
| 6,536,536 B1 * | 3/2003 | Gass | B23B 31/123 173/171 |
| D490,152 S | 5/2004 | Myall et al. | |
| 7,185,562 B2 * | 3/2007 | Raines, Jr. | A61B 17/1624 81/429 |
| D559,385 S | 1/2008 | Boone et al. | |
| D560,805 S | 1/2008 | Young et al. | |
| 7,441,480 B2 * | 10/2008 | Raines, Jr. | A61B 17/1624 173/178 |
| 7,942,617 B2 * | 5/2011 | Allemann | B24B 23/02 173/221 |
| 8,747,392 B2 | 6/2014 | Le et al. | |
| D715,936 S | 10/2014 | Darian | |
| D731,057 S | 6/2015 | Gitman | |
| D733,876 S | 7/2015 | Rydberg et al. | |
| D740,939 S | 10/2015 | Canady et al. | |
| D744,644 S | 12/2015 | Lee et al. | |
| D746,460 S | 12/2015 | Gitman | |
| D770,044 S | 10/2016 | Fiksen et al. | |
| D775,338 S | 12/2016 | Gitman | |
| D794,193 S | 8/2017 | Schuerg | |

(Continued)

*Primary Examiner* — Zade Coley
(74) *Attorney, Agent, or Firm* — Norton Rose Fulbright US LLP

(57) ABSTRACT

A power-driven surgical tool that includes an elongated housing having a fin member aligned substantially parallel with the longitudinal axis of such elongated housing. The tool is power-driven and enables the attachment of either a drill bit or a screwdriver bit. The configuration is such as to provide maximum comfort and a visualization of the target area for the surgeon.

34 Claims, 18 Drawing Sheets

(56) References Cited

U.S. PATENT DOCUMENTS

| | | | |
|---|---|---|---|
| D802,769 S | | 11/2017 | Robertson et al. |
| D818,584 S | * | 5/2018 | Lee et al. |
| 2005/0152759 A1 | * | 7/2005 | Allemann ............... B24B 23/02 |
| | | | 409/181 |
| 2005/0268750 A1 | * | 12/2005 | Bruce .................. A61B 17/866 |
| | | | 81/52 |
| 2006/0117911 A1 | * | 6/2006 | Raines, Jr. ......... A61B 17/1624 |
| | | | 81/52 |
| 2007/0125201 A1 | * | 6/2007 | Raines, Jr. ......... A61B 17/1624 |
| | | | 81/52 |
| 2014/0288536 A1 | | 9/2014 | Le et al. |
| 2014/0296845 A1 | * | 10/2014 | Miller ................ A61B 18/1492 |
| | | | 606/41 |
| 2017/0348037 A1 | * | 12/2017 | Sexson .............. A61B 17/1626 |
| 2018/0078298 A1 | | 3/2018 | Gonzalez et al. |

* cited by examiner

POWER DRIVEN SURGICAL TOOL

TECHNICAL FIELD

The present invention relates generally to a handheld surgical tool. More particularly, the present invention relates to a handheld surgical tool capable of either drilling into a bone or installing screws into the bone, the tool having an elongated configuration with a fin element permitting the surgeon to hold the tool in a pencil-grip.

BACKGROUND OF THE INVENTION

Prior to the present invention, prior art devices require that the surgeon using a handheld drill grip the device firmly prior to rotation for either rotating a drill bit or a screwdriver. Typically, these devices are used to drill holes or insert screws through very thin bone and need to be particularly responsive to immediate penetration of the bone. Additionally, the surgeon needs an open and clear view of the target area when drilling a hole or rotating a screw. Such prior art devices are frequently cumbersome to hold and inhibit a clear target, unless the surgeon moves into an awkward position above or beside the tool for visual inspection of the target area as the drilling occurs. In an effort to overcome these issues, prior art devices have included pistol-grip handles, such as the MatrixPRO Driver manufactured by DePuy Synthes, model number 05.000.020. Additionally, other configurations have evolved, such as the BOS System, manufactured by KLS Martin, model number 50-800-01-07, and the configuration disclosed in U.S. Pat. No. 8,747,392.

Therefore, the need exists for a pencil-grip configured power driver having a geometrical arrangement that provides the surgeon with a comfortable and firm grasp and also a clear view of the target area. In addition, any such device should be battery operated to minimize tethers extending from the unit. Since it is a surgical tool, it must be manufactured of suitable FDA approved material and capable of being sterilized in an autoclave, for example.

BRIEF SUMMARY OF THE INVENTION

The present invention is a surgical tool having a pencil-grip, elongated housing. This housing includes a fin member disposed proximal to the distal end of the housing and positioned substantially coplanar with the longitudinal axis of the housing. In this manner, the surgeon may grip the unit in a pencil-grip grasp with the fin resting against the surgeon's second finger for enhanced stability during operation. The present invention includes a removable battery source. A motor is positioned within the elongated housing and receives electrical power from the battery source. A drive head is positioned at the distal end of the tool in rotational communication with the motor. The drive head is configured to engage an attachment piece. In this manner, the surgeon may hold the tool in a pencil-grip manner with the fin stabilizing the housing during the operation. With an attachment piece in the tool and a battery installed, the center of gravity of the tool is located proximal to the fin so that during operation the tool rests comfortably in the "V" of the surgeon's hand, between the base of the thumb and the index finger. In this manner, the surgeon may easily control the drive head with a switch positioned proximal to the end of the surgeon's index finger.

The surgical tool may include a sensor that samples the draw by the motor during its operation when the attachment piece includes a bit to drive a screw, and a controller that receives a signal from the sensor indicative of the draw by the motor. The controller uses those signals to determine the torque being applied to the bit that engages a screw to provide torque-limiting capability so as to immediately stop the rotation of the screw when a particular torque is sensed.

The present invention also comprises a removable power source having a battery housing and a battery supported within the housing. The housing includes interlocking rails for slidable engagement and locking of the battery housing to the workpiece, in this instance, the surgical tool. The housing includes displaceable connector pins in electrical communication with the battery, the pins being displaceable in a direction that is generally substantially parallel with the longitudinal axis of the battery housing. In this manner, the removable power source may be interlockably engaged with a surgical tool having a pencil-grip, elongated housing and a fin member disposed proximal to the distal end of the housing substantially coplanar with the longitudinal axis of the housing, as described above.

BRIEF DESCRIPTION OF THE DRAWINGS

For a more complete understanding of the present disclosure and its advantages, reference is now made to the following descriptions, taken in conjunction with the accompanying drawings, in which.

DETAILED DESCRIPTION OF THE INVENTION

Figures 12, 12A:
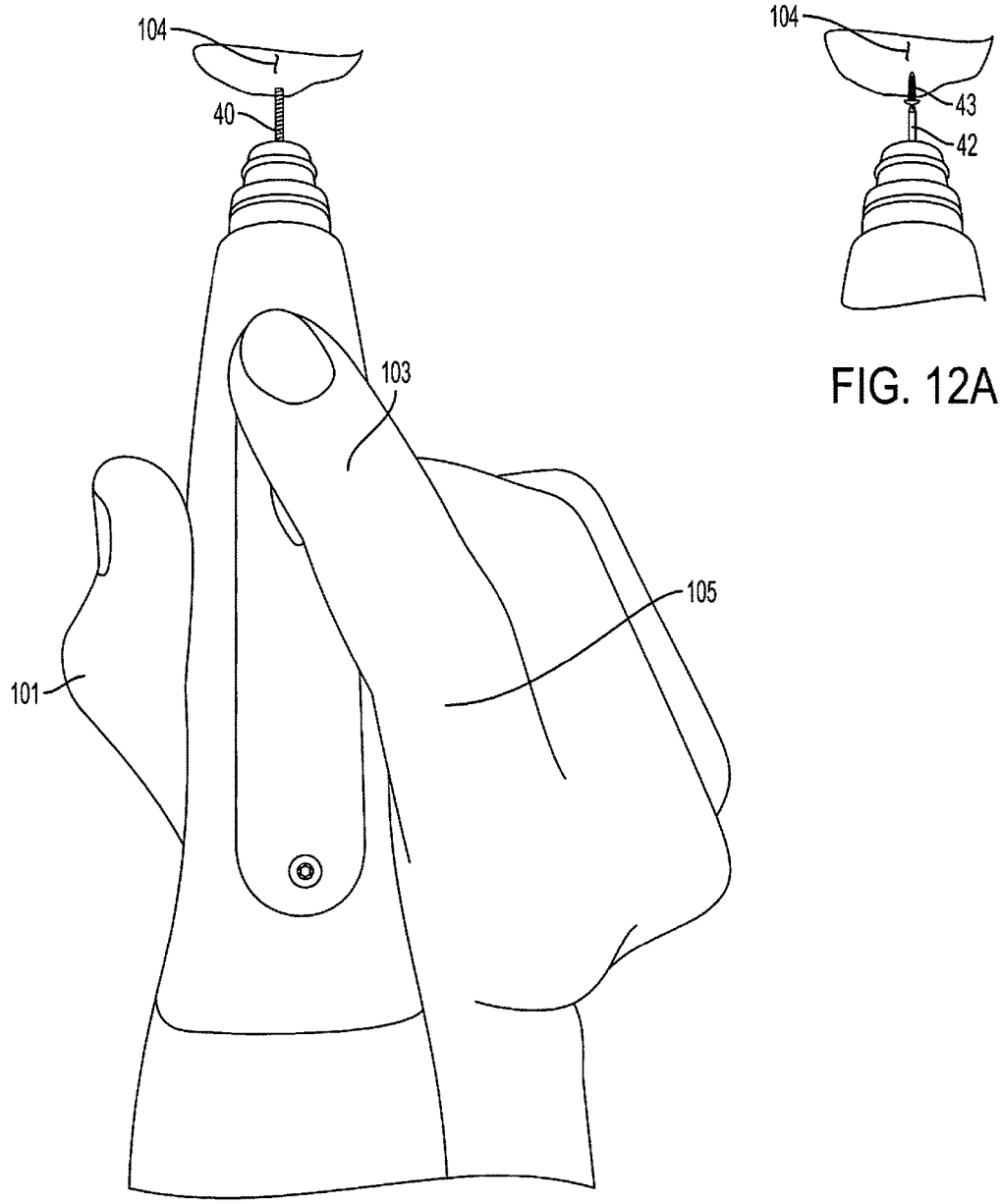
FIG. 12 is a rendition of a surgeon's hand holding the preferred embodiment of the present invention from a top view.
FIG. 12A is a partial rendition of the present invention showing the rotation of a screw bit rotating a screw into a target area.
Figure 13:
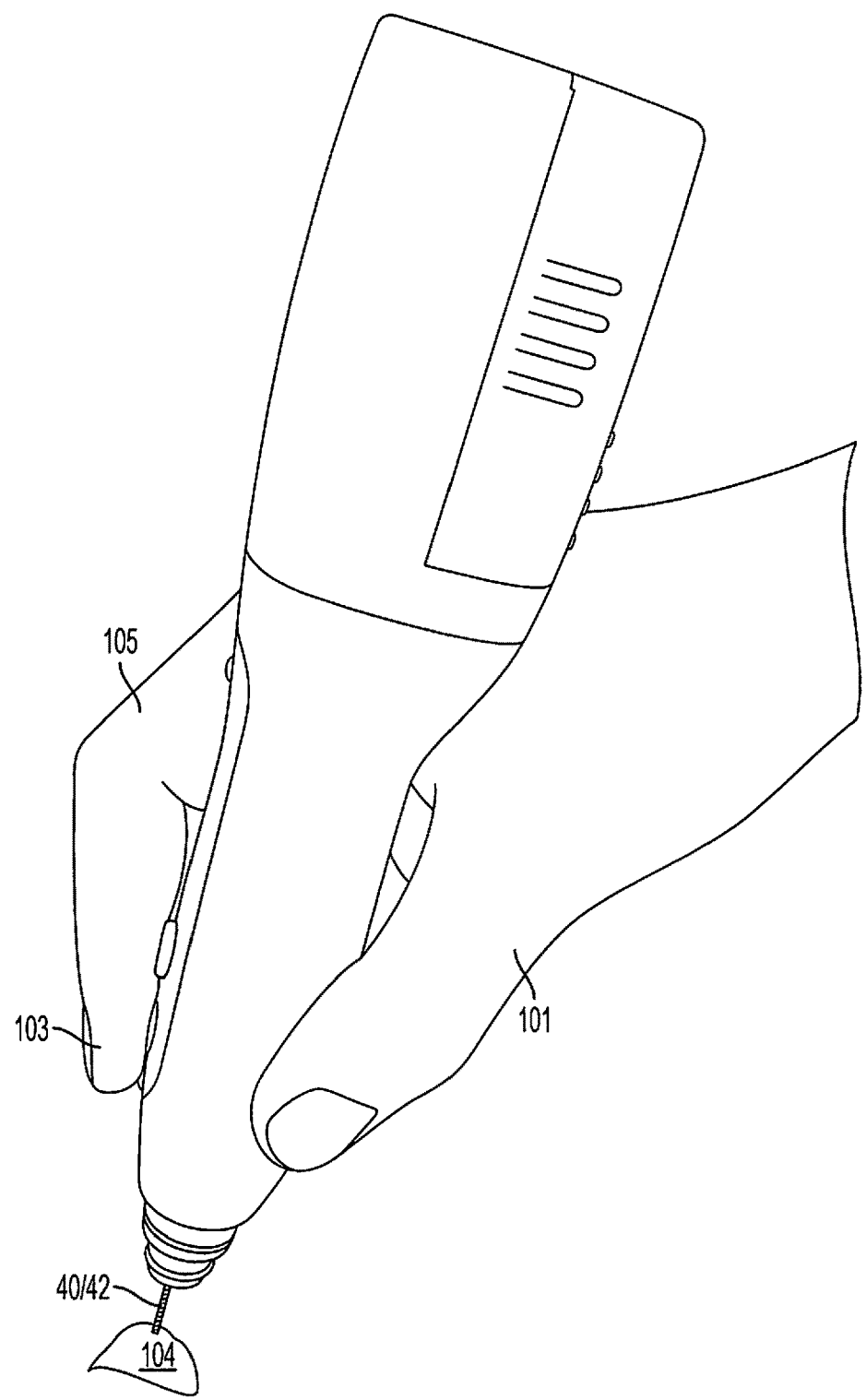
FIG. 13 is a rendition of the surgeon's hand holding the preferred embodiment of the present invention from an elevation view.

Referring to FIGS. 1-4, FIG. 1 is a perspective view of the preferred embodiment of the power-driven surgical tool 30 having a pencil-grip elongated housing 32 with a proximal end 36 and a distal end 34. A drive head 38 is positioned at the distal end 34 of the tool 30. The drive head is rotated by a motor, which is described in more detail below. The drive head is, in turn, adapted to connect to various attachment pieces, such as a drill bit, as illustrated in FIGS. 12 and 13, or a screw driver. A battery housing 44 is supported by the elongated housing 32 at the proximal end 36.

Figure 16:
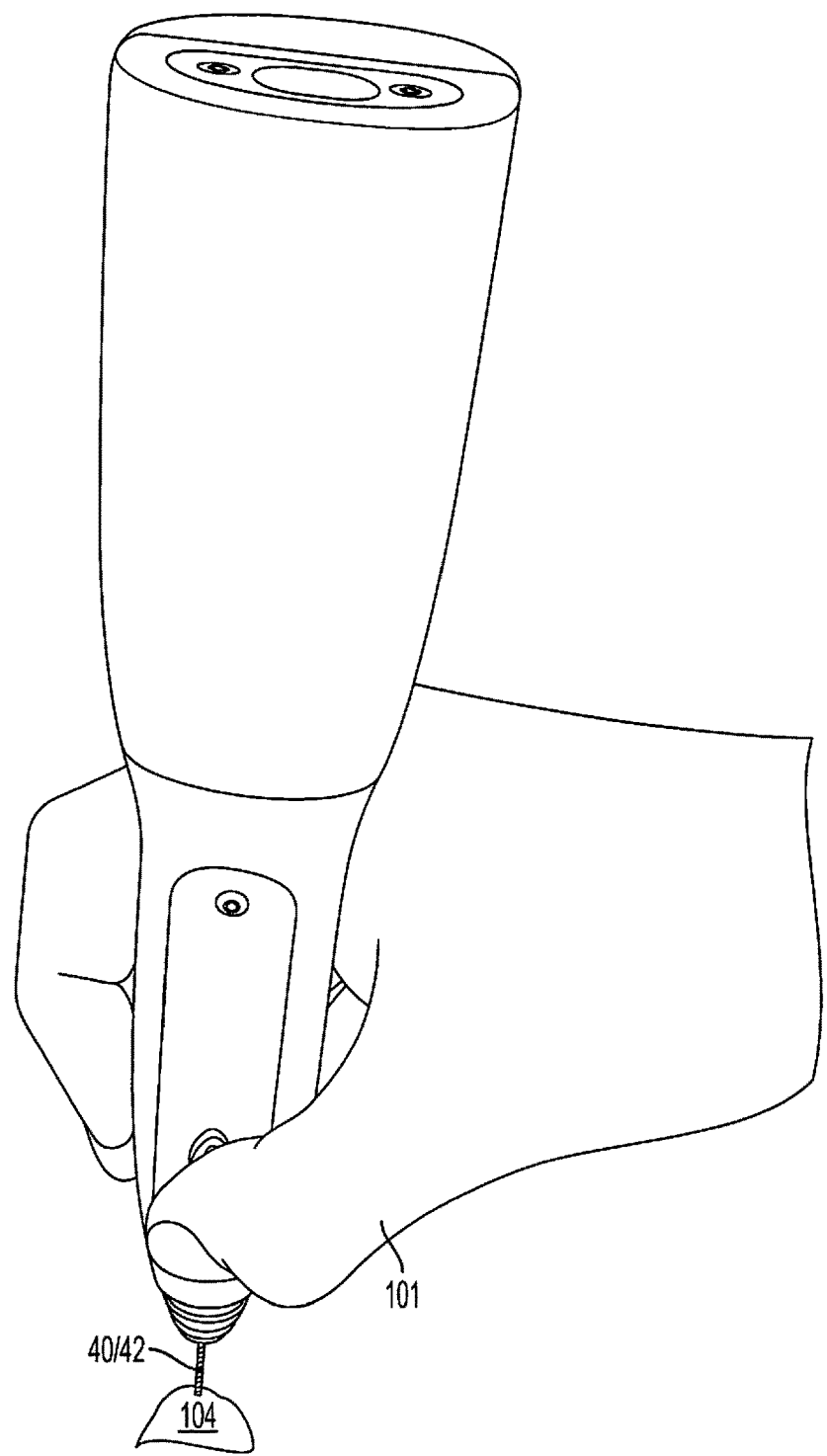
FIG. 16 is a rendition of the surgeon's hand gripping the preferred embodiment of the present invention with the thumb engaging the forward and reverse switches.
Figure 17:
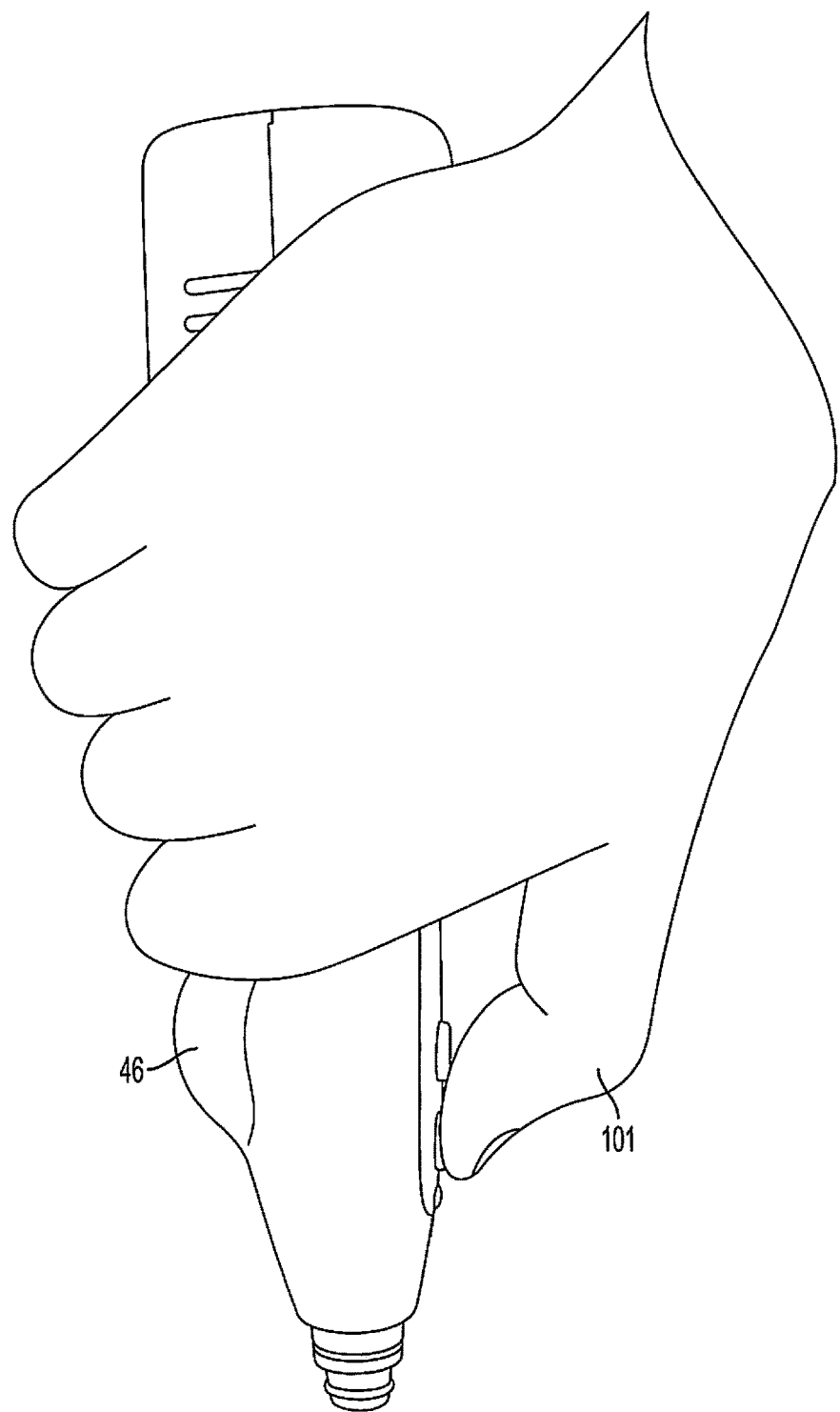
FIG. 17 is a rendition of the surgeon's hand holding the preferred embodiment of the present invention with the thumb engaging the forward and reverse switches, and the fingers supporting the underside of the preferred embodiment of the present invention.

Referring still to FIGS. 1-4, elongated housing 32 includes a fin 46 that is substantially coplanar with a longitudinal axis 48 of housing 32. Housing 32 includes an expanding region 50 so that the exterior configuration of housing 32 provides a region 56 proximal to fin 46. Region 56 is configured so that tool 30 can be comfortably supported by the surgeon's hand, preferably in the V of the hand between the base of the thumb and the index finger, as shown in FIGS. 16 and 17. Furthermore, the weight of tool 30 is configured so that the center of gravity 57 of tool 30 is preferable within region 56. In this manner, the tool 30 may comfortably rest within the surgeon's hand, again preferably within the V of the surgeon's hand between the base of the thumb 101 and the index finger 105 (see FIGS. 16 and 17). As used in this patent application, the index finger is the first finger by the thumb. The second finger is adjacent to the index finger. Thus, a hand has a thumb and four fingers.

Figure 1:
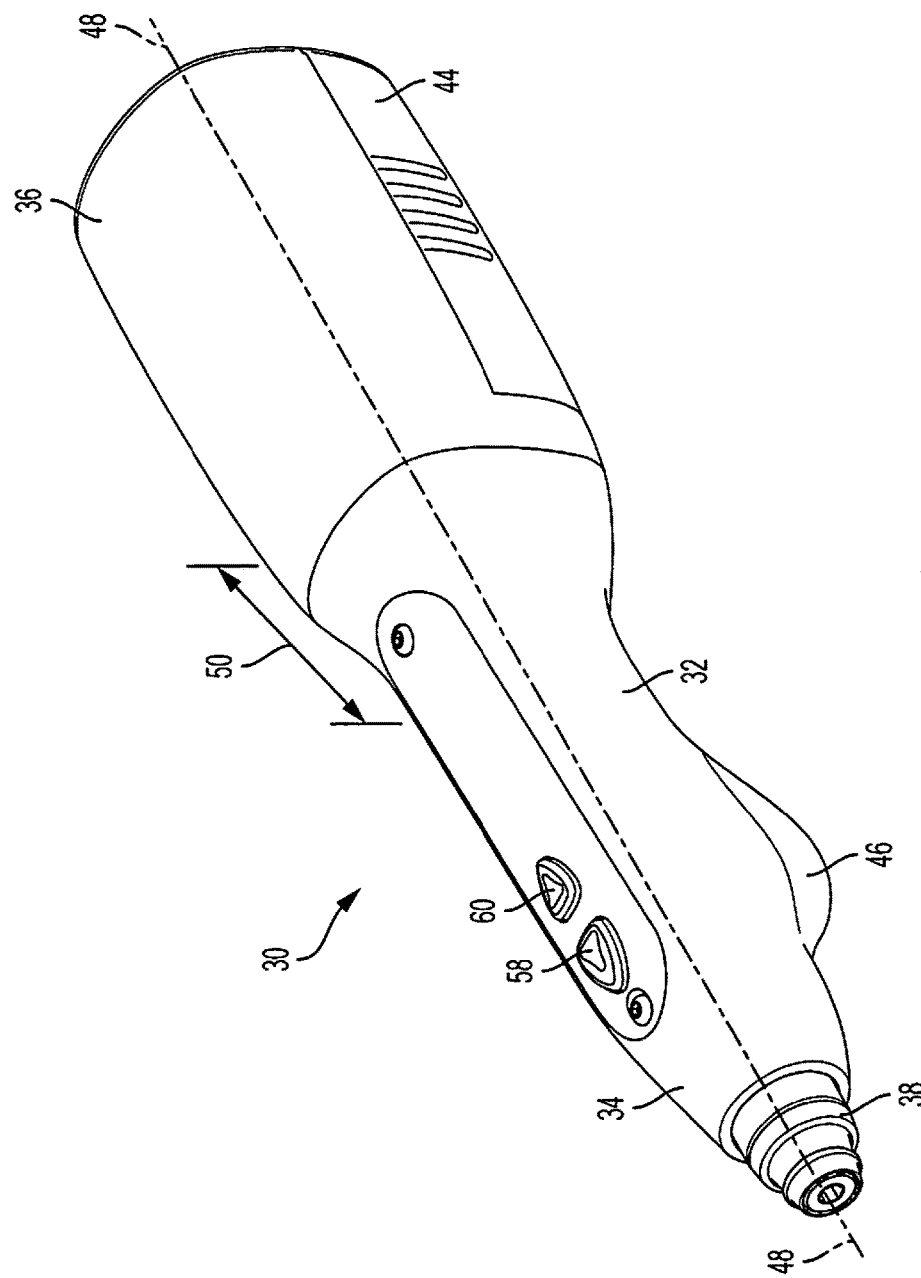
FIG. 1 is a perspective view of the preferred embodiment of the present invention.
Figure 2:
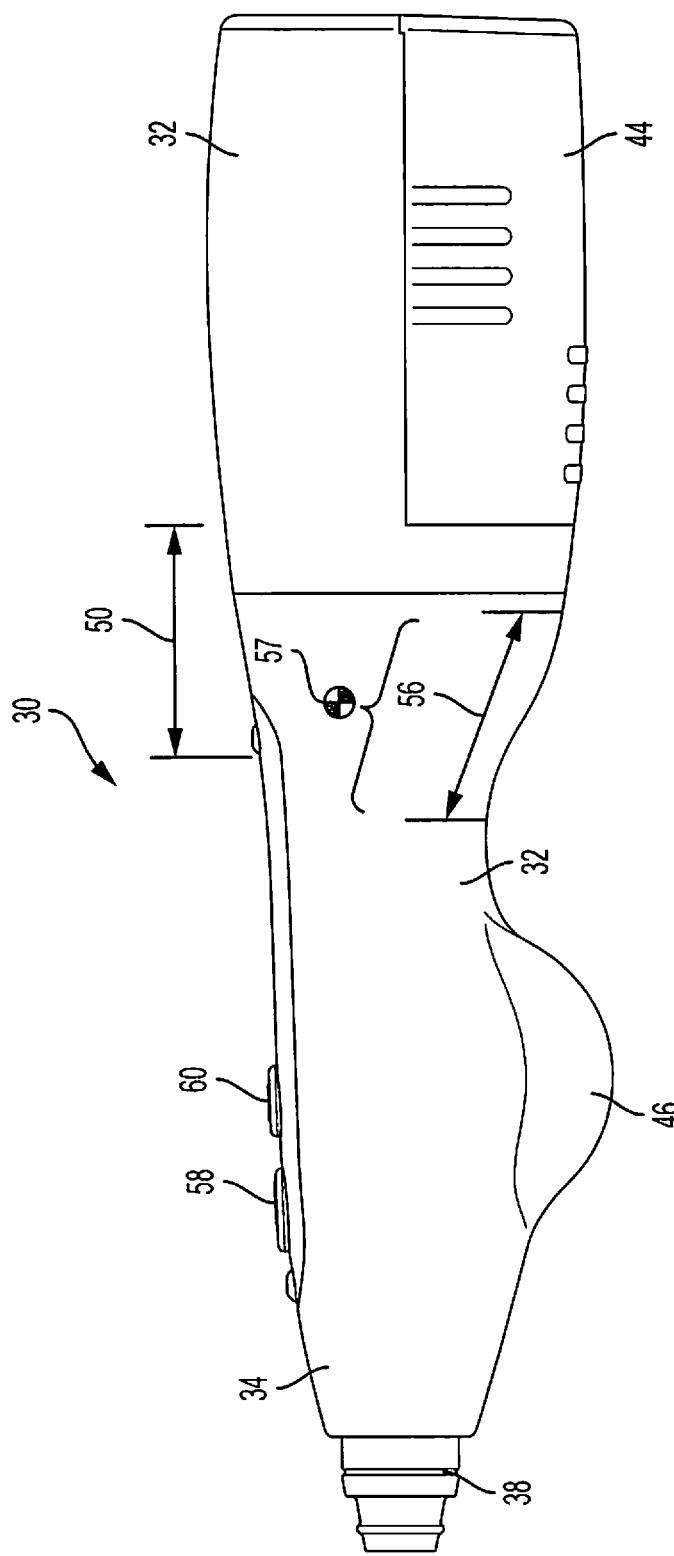
FIG. 2 is an elevation view of the preferred embodiment of the present invention.
Figure 3:
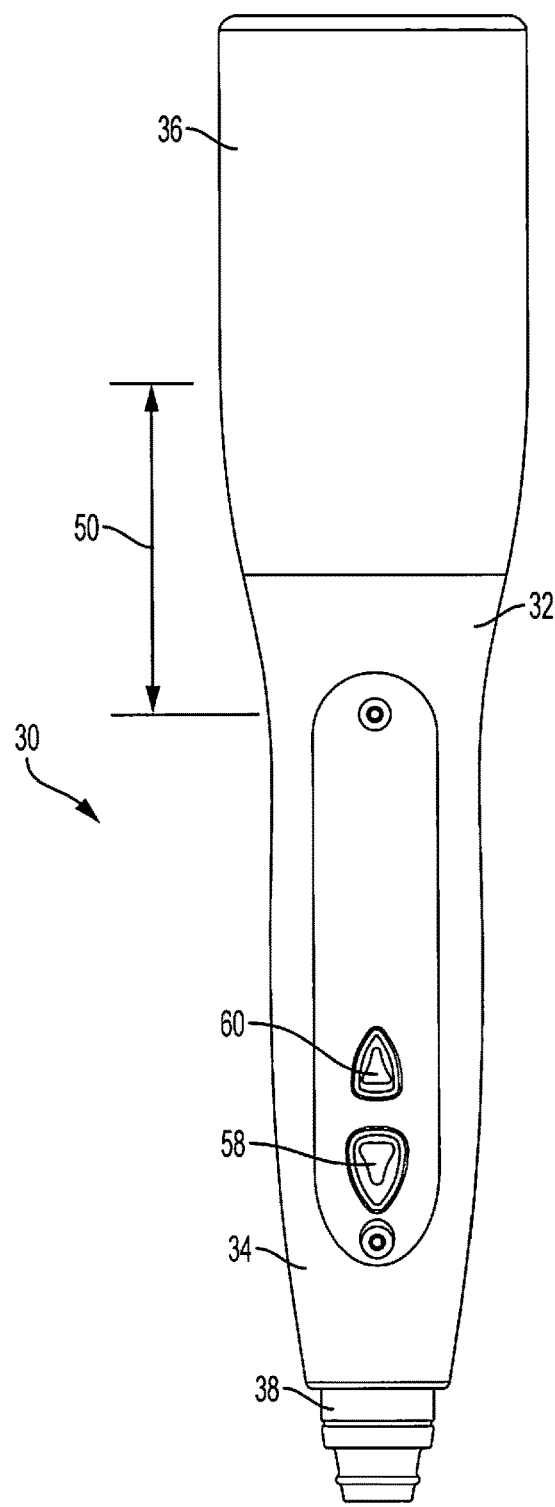
FIG. 3 is a top view of the preferred embodiment of the present invention.
Figure 4:
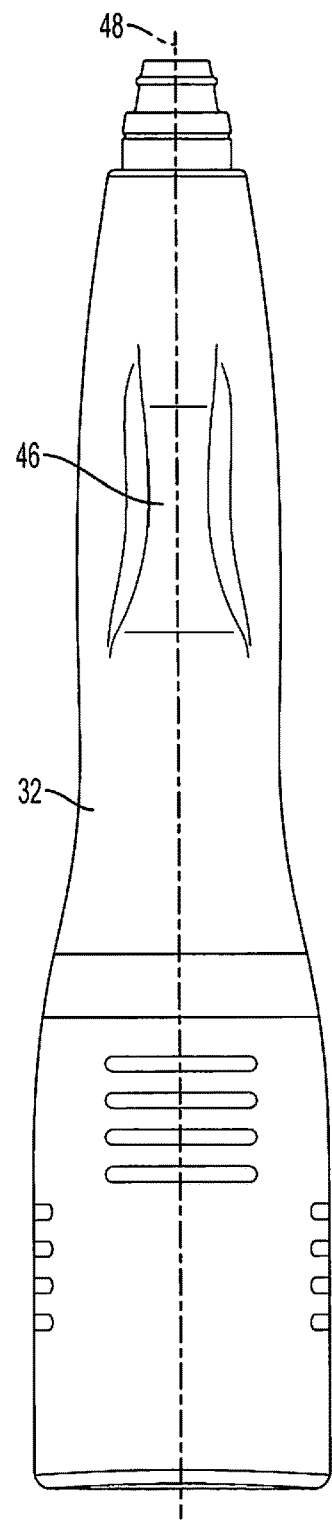
FIG. 4 is a bottom view of the preferred embodiment of the present invention.

Referring FIG. 1, rotation of drive head 38 is controlled in the forward position by depressing button 58 and in the reverse position by depressing button 60. Thus, referring briefly to FIG. 12, it can be seen that once the present invention is assembled and comfortably held within the surgeon's hand with tool 30 resting within the V of the surgeon's hand between the base of the thumb 101 and the index finger 105, the index finger tip 103 may be used to engage either button 58 or 60 to rotate an attachment piece, such as a drill bit (see FIG. 12) or a screw driver within drive head 38 clockwise or counter-clockwise. It is noted that, in an embodiment, button 58 and button 60 may be replaced by a switch, where the switch may be placed in a first state or a second state to control rotation of the drive head 38 in forward and reverse directions.

Referring back to FIGS. 12-15, the above described configuration of the elongated housing 32 enables tool 30 to be held in a pencil-grip by the surgeon. The fin 46 rests comfortably between the surgeon's thumb 101 and his second finger 102. In this manner, the surgeon can firmly grasp fin 46 to prevent rotation of the tool 30, as shown in FIG. 12-15, and tool 30 may comfortably rest in the V of the surgeon's hand between the base of the thumb and the index finger as show in FIGS. 12-13. This preferred configuration reveals the target area 104. Thus, due to the pencil-grip configuration the surgeon has clear visibility of target area 104, with no interference from other portions of the surgeon's hands or tool 30.

Figure 5:
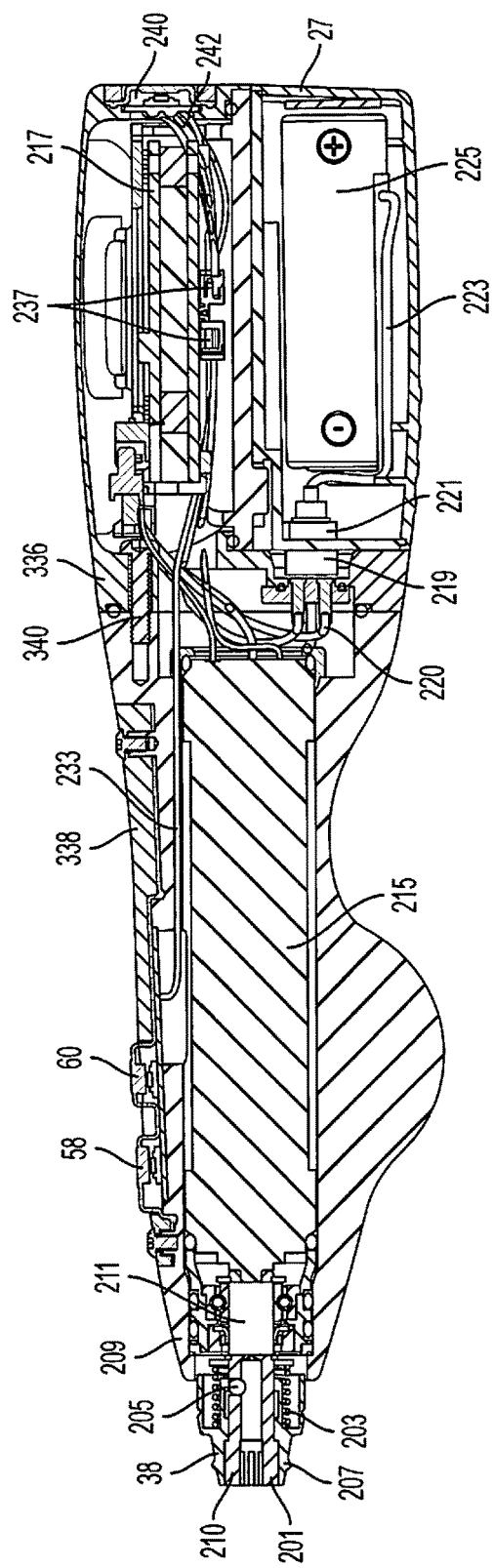
FIG. 5 is a cross-sectional view of the preferred embodiment of the present invention taken along line 5-5 of FIG. 3.
Figure 6:
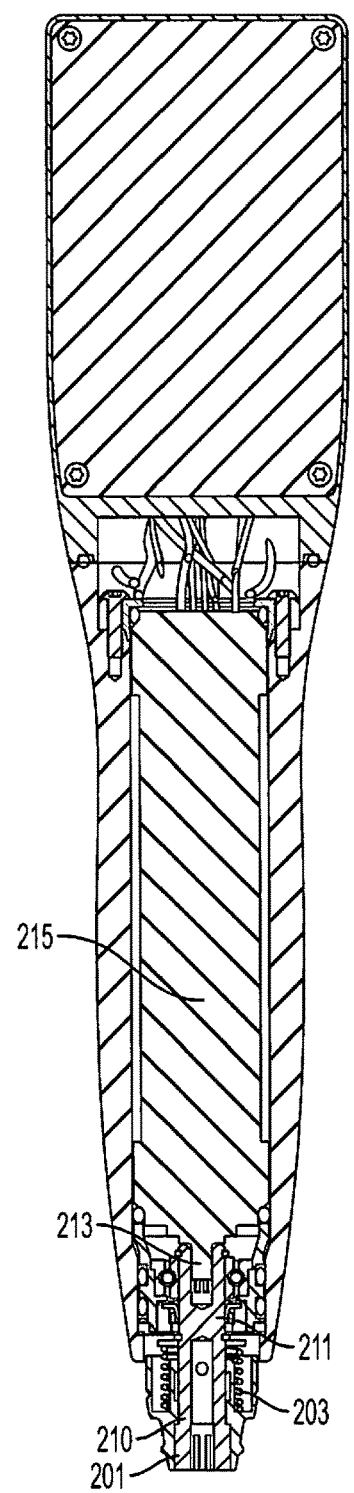
FIG. 6 is a cross-sectional view of the preferred embodiment of the present invention taken along line 6-6 of FIG. 2.
Figure 7:
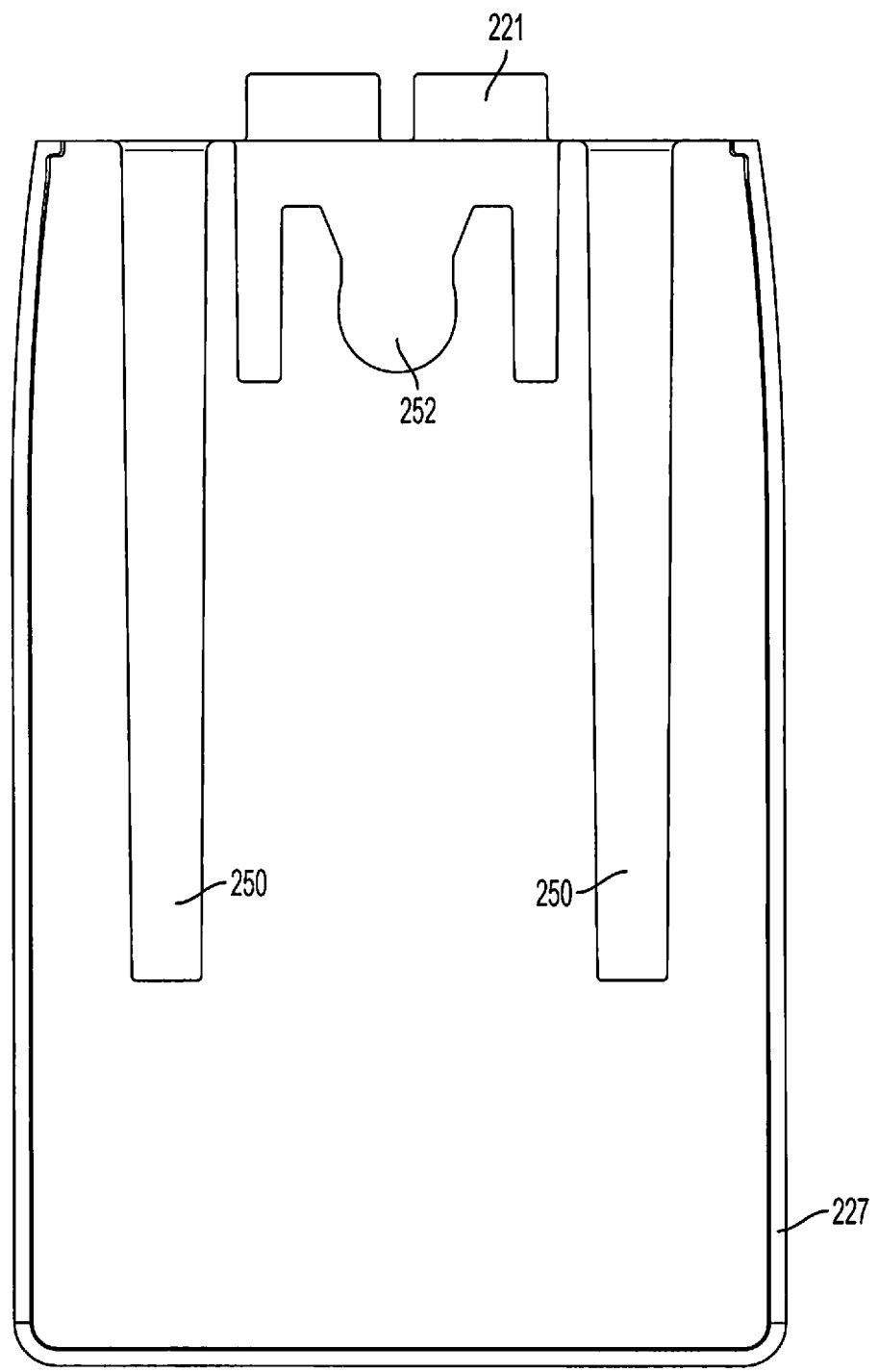
FIG. 7 is a top view of the battery compartment of the preferred embodiment of the present invention.
Figure 8:
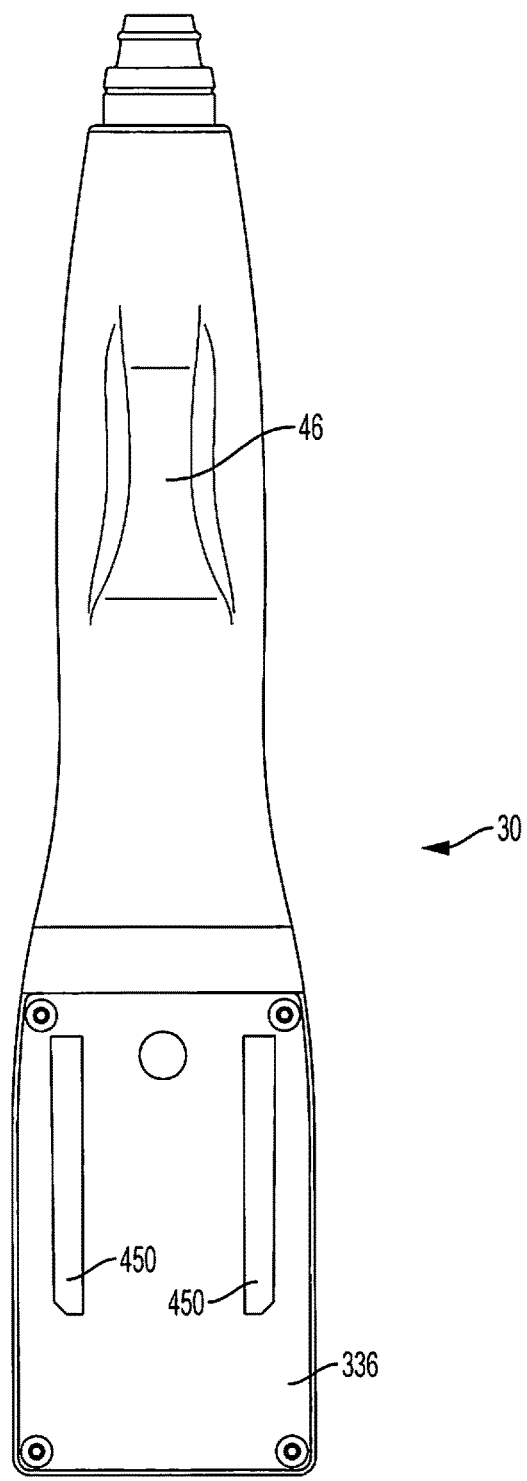
FIG. 8 is a bottom view of the elongated housing of the preferred embodiment of the present invention with the battery compartment removed.
Figure 9:
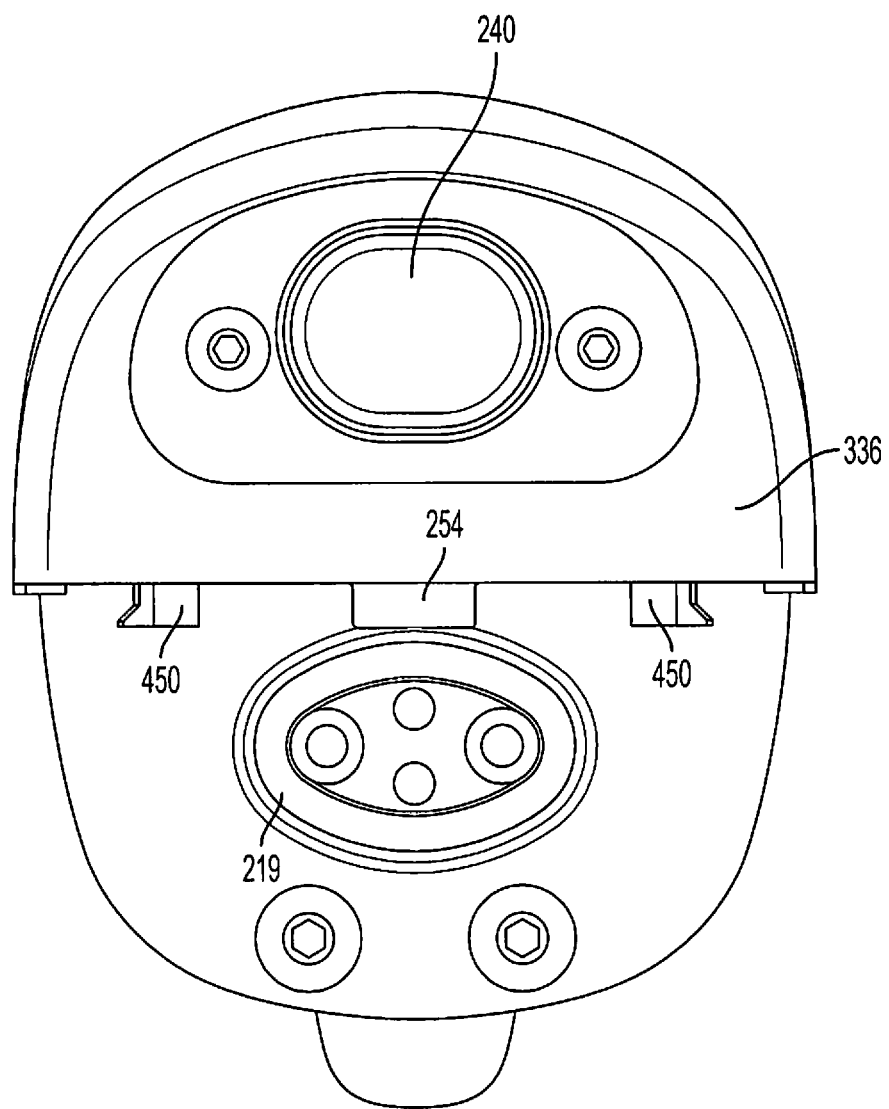
FIG. 9 is an end view of the elongated housing of the preferred embodiment of the present invention with the battery compartment removed.
Figure 10:
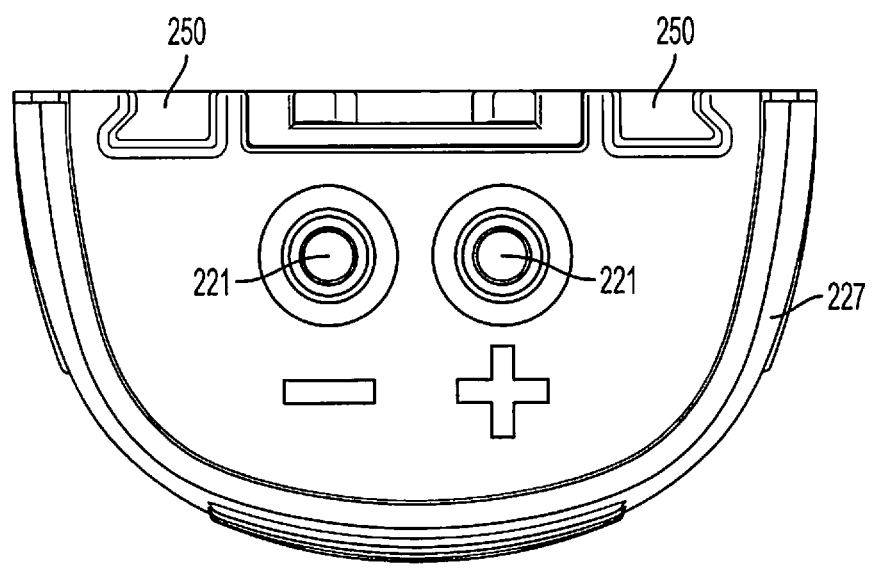
FIG. 10 is an end view of the battery compartment of the preferred embodiment of the present invention.
Figure 11:
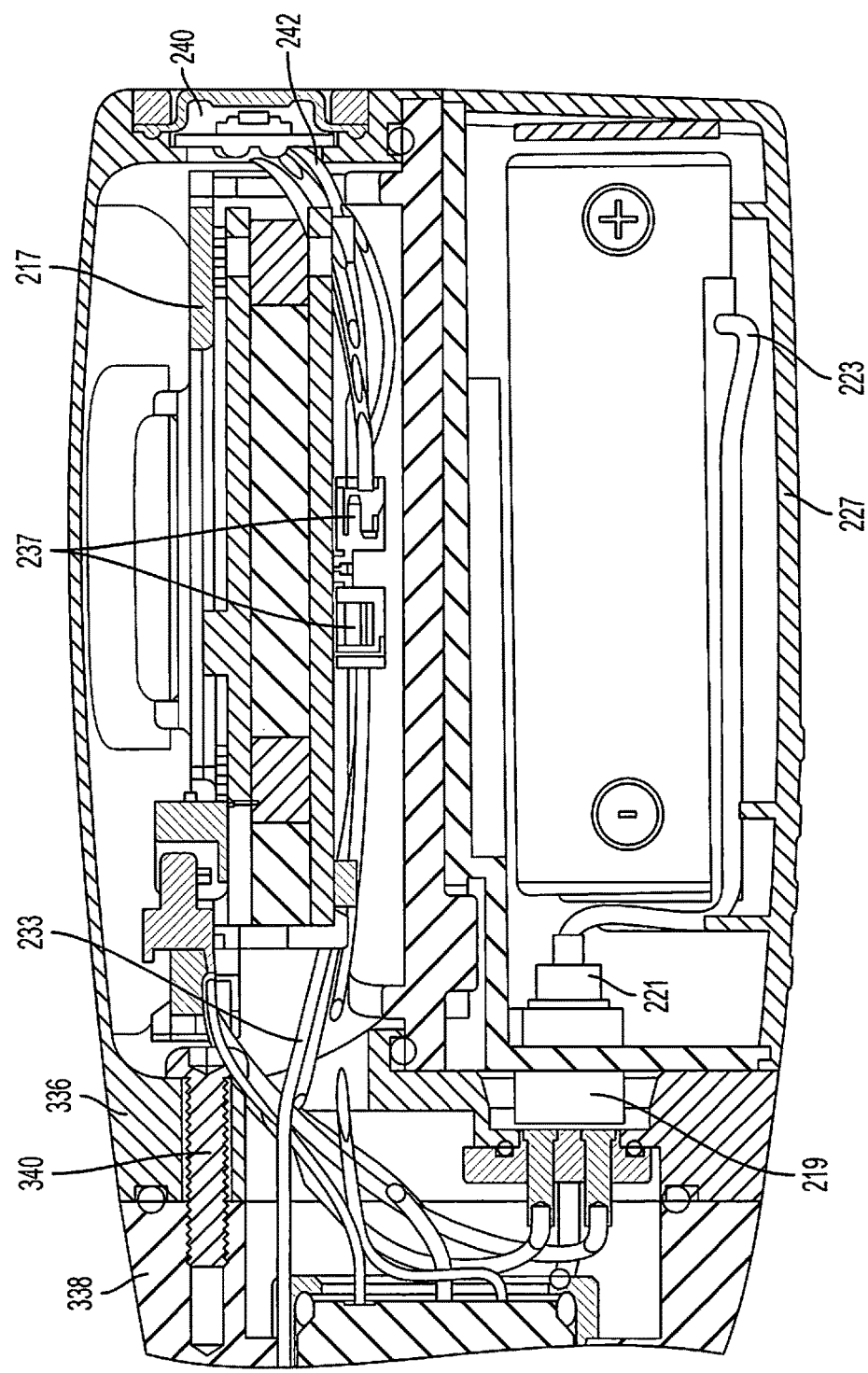
FIG. 11 is a detail cross-sectional view of the proximal end of the present invention as shown in FIG. 5.

Referring now to cross-sectional views shown in FIGS. 5 and 6, Housing 32 is made up of a proximal housing 336 and a distal housing 338. Proximal and distal housings 336/338 may be connected via a screw or other interlocking arrangement generally reflected by 340 and well known to those skilled in the art. Drive head 38, located at distal end 209 of distal housing 338, includes a collet shaft 201 advanced forward by a spring 203. A bearing 205, positioned with shaft 201, serves to contact the selected attachment piece, such as a drill bit (see FIG. 12) or a screw driver. Such drive heads are well known to those skilled in the art to engage a surgical attachment piece. The attachment piece may include an embedded sensor that signals the drive head of its purpose, i.e. for drilling purposes only and not to rotate a screw which would engage the torque-limiting feature of the present invention, as discussed further below. Collet shaft 201 fits within collet sleeve 207. The distal end 210 of collet shaft 201 would engage the attachment piece, while the proximal end 211 of collet shaft 201 is in communication with the motor drive shaft 213 of motor 215. Motor 215 may be a brushless DC slotted motor, such as that manufactured by PORTESCAP as model number B0614H4041. Motor 215 is in electrical communication with a printed circuit board 217, which may include or be coupled to a processor. Printed circuit board 217 may, in turn, be in communication with battery plate 219 via connector 220. Plate 219 may, in turn, be in communication with battery connector pins 221 that have leads 223 extending back to battery cells 225. The battery connector pins 221, battery leads 223, and battery cells 225 are supported within removable battery housing 227. Forward button 58 and reverse button 60 are in communication with battery plate 219 via connector 235 to printed circuit board 217 through switches 237. In this manner, depression of forward button 58 will cause the rotation of motor drive shaft 213 of motor 215 in a particular rotational direction, while depression of reverse button 60 will cause the opposite rotation of motor drive shaft 213.

In the operation of surgical tool 30, it may be desirable to bypass a torque-limiting feature of the invention as described in more detail below as shown in FIGS. 12-15, permitting the surgeon to use tool 30 as a drill. To accomplish this, a button 240 may be depressed that, through leads 242, engages the printed circuit board 217 to bypass the torque-limiting feature and permit the forward 58 or reverse 60 buttons to operate without the torque-limiting feature. Switch 240 may be described from time to time as a mode switch, enabling the surgeon to switch the operational mode from a drill to a screw driver.

Referring now to FIGS. 7-11, battery housing 227 supports connector pins 221 extending therefrom. The battery connector pins 221 are adapted to be displaced or depressed in a longitudinal direction substantially coplanar with longitudinal axis 48 of tool 30. Once extended connector pins 221 are, in turn, engageable with contact plate 219. Connector pins 221 communicate through connectors 223 to the positive and negative terminals of battery cell 225. Housing 227 also includes interlocking rails 250 that are adapted to engage corresponding interlocking rails 450 of the exterior housing, preferably the proximal exterior housing 336. The interlocking rails may be a tongue-in-groove or dovetail interlocking that provides a very snug fit once the housing 227 is slid within proximal housing portion 336. Once battery housing 227 is slid longitudinally within proximal housing portion 336 contact is made between and contact plate 219. Engagement is confirmed because the connector pins 221 are displaceable inwardly relative to the connector plate, ensuring contact. Battery housing is held in position by a clasp 252 which engages a detent 254 supported by the exterior proximal housing 336 of elongated housing 32. Battery cell 225 is preferably a high power primary Lithium Metal Oxide cell such as that manufactured by TADIRAN BATTERIES, model TLM-1550HE, or suitable equivalent. It is preferable that such batteries have a shelf life of at least 60 months to ensure their functionality once used in an operation. Typically, the battery would not be rechargeable, but merely disposed of following use. However, it may be advantageous at times that such batteries may be rechargeable. In such event a nickel cadmium may be appropriate. Any such recharging of the battery unit might be handled through contact with displaceable connector pins 221 and the recharging system.

When the present invention is to be used as a screwdriver, the motor 215, as discussed above, connects to the drive head 38. Drive head 38 can receive an attachment screw driver bit, such as a crosshead bit, flathead bit, star bit (e.g., Torx), socket bit (e.g., hex), or otherwise. The bit in turn can be interfaced with a screw 442 having a head with a corresponding shape. Thus, the screw can be positioned at a desired insertion target area on a substrate (e.g., a bone) and the motor drive shaft 213 can be operated to drive the screw into the substrate.

In an embodiment, tool 30 may utilize torque limiting techniques that enable the tool 30 to monitor and/or limit the torque that it is applied to the screw during the insertion process. For example, tool 30 can include a sensor that senses the torque of a motor of the tool 30 (e.g., the motor 215 of FIG. 5). The sensor can send such data to a controller. In an embodiment, the controller may include a processor coupled with a memory. In certain variants, the controller is configured to determine or receive signals indicative of one or more of the following data features: current supplied to the motor, number of revolutions of the screw and/or motor, distance traveled by the screw (e.g., into the bone), speed of the motor, or otherwise. In an embodiment, one or more of the components (e.g., the sensor, processor, memory, controller, and the like) utilized to provide the torque limiting functionality may be included within, or coupled to, the printed circuit board 217 discussed above with reference to FIG. 5. In an additional or alternative embodiments, instructions may be stored in the memory of the tool 30 as program code that may be executed by the processor to perform various operations, such as determining a torque limit, instructing the motor to cease operation, instructing a power source to reduce and/or stop providing power to the motor, or other operations. Additional aspects of providing torque limiting techniques may be found in U.S. Pat. No. 9,265,551.

Typically, to remove the screw from the bone, and to free the plate, tool 30 can be interfaced with the head of the screw and the rotation of the screw reversed. Because the screw is not cutting into the bone and is not being tightened against the bone or plate, the torque on the screw during a removal operation is normally less than during the insertion process described above.

With respect to the torque-limiting capability of some embodiments of the invention, it may be desirable that the unit have the capability of high rotational speed in excess of 2000 rpm when in a drill mode and as low as 225 rpm when in a screwdriver mode. Switch 240 may be designed to provide forward rotation of 2000 rpm with 0-30 inch-ounces in torque (0-21 N-cm). The reverse mode may operate in the range of about 225-325 rpm for approximately one to two seconds and would preferably then terminate. The reverse mode may be resumed by depressing button 60. Again, in the reverse mode, it is preferable that the unit provides between 10-15 inch-ounces torque (7-11 N-cm). In the forward mode, it is desirable that the unit be capable of providing at least 30 inch-ounces in torque (21 N-cm), more preferably 20-30 inch-ounces in torque (14-21 N-cm), and most preferably 0-10 inch-ounces if torque (0-7 N-cm) for thin or delicate bone structure, such as that found in the cranial macular area.

Operational Use of the Present Invention

Referring now to FIGS. 12-18, the various handheld configurations of the present invention by the surgeon will now be described. Referring in particular to FIGS. 12-15, the pencil-grip mode is demonstrated wherein the surgeon grasps the unit so that fin 46 is between the thumb 101 and the distal end 103 of the index finger 105, as shown in FIGS. 12-13. As noted above, in this manner, the unit may be held firmly by the surgeon, yet also maintained in a comfortable position since the center of gravity 57 provides that the unit will rest in the V of the surgeon's hand between the base of the thumb and the index finger as described above. In this manner, the unit is in balance and in a comfortable and maneuverable position, permitting the surgeon to use tool 30 over an extended period of time. In addition, as illustrated further in FIGS. 12-13 and 15, retaining the invention in a pencil-grip format provides a substantial and preferable view of the target area 104. The surgeon need not look around the unit in an awkward manner, but may maintain a somewhat erect posture for comfort and convenience.

Figure 15:
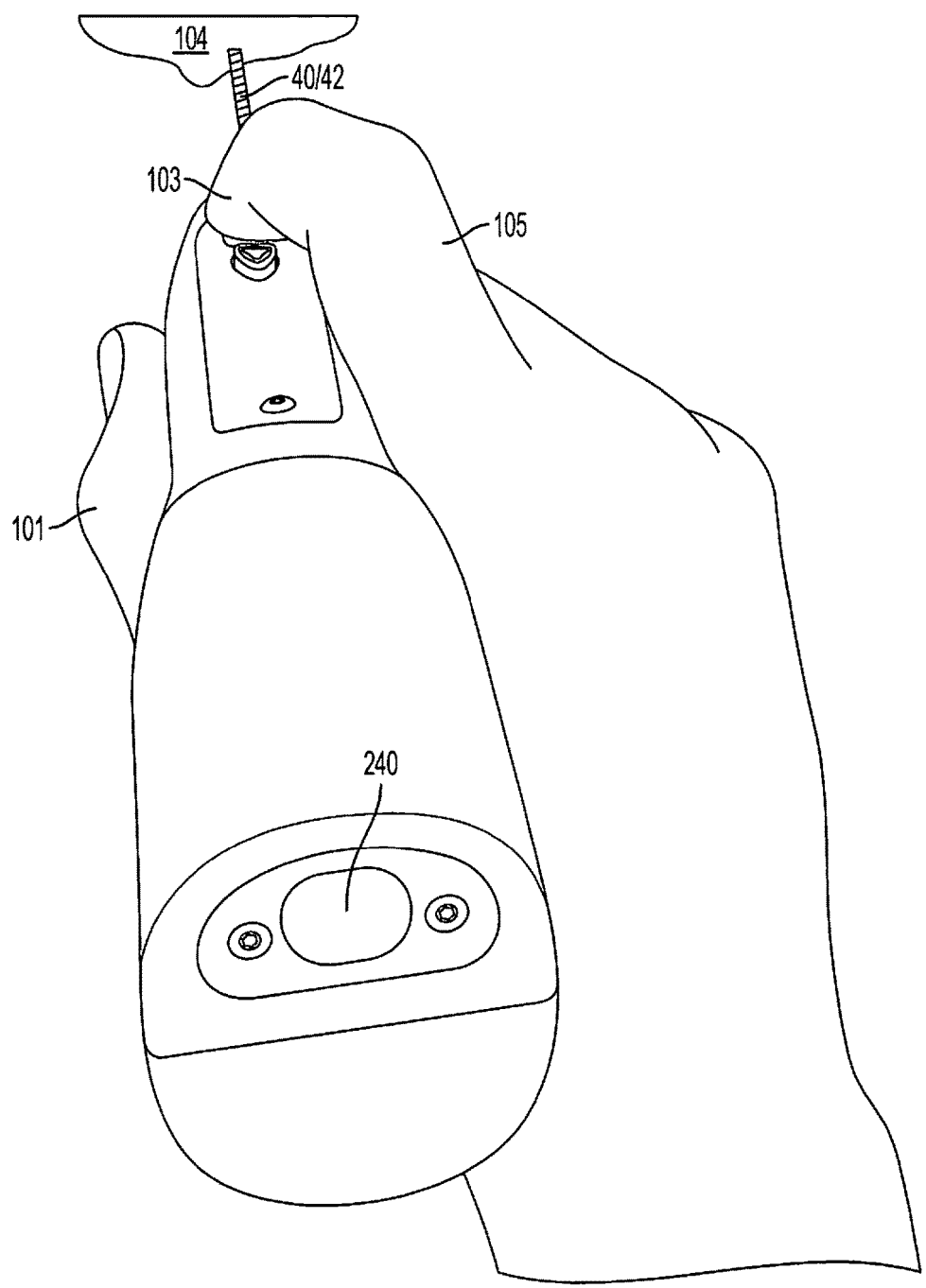
FIG. 15 is a rendition of the surgeon's hand holding the preferred embodiment of the present invention from a top and back view at approximately a 45° angle.

Referring still to FIGS. 12-13 and 15, the present invention is shown in the pencil-grip format with the distal end 103 of the index finger 105 depressing either the forward button 58 or the rear button 60 and having the attachment either be a drill 40, as shown in FIG. 12, or a screw driver bit 42, as shown in FIG. 12A. If a screw bit is used, the torque-limiting feature of the present invention is an operation, as described above. Otherwise, if a drilling mode is desirable, the surgeon would depress switch 240, bypassing the torque-limiting capability.

Figure 14:
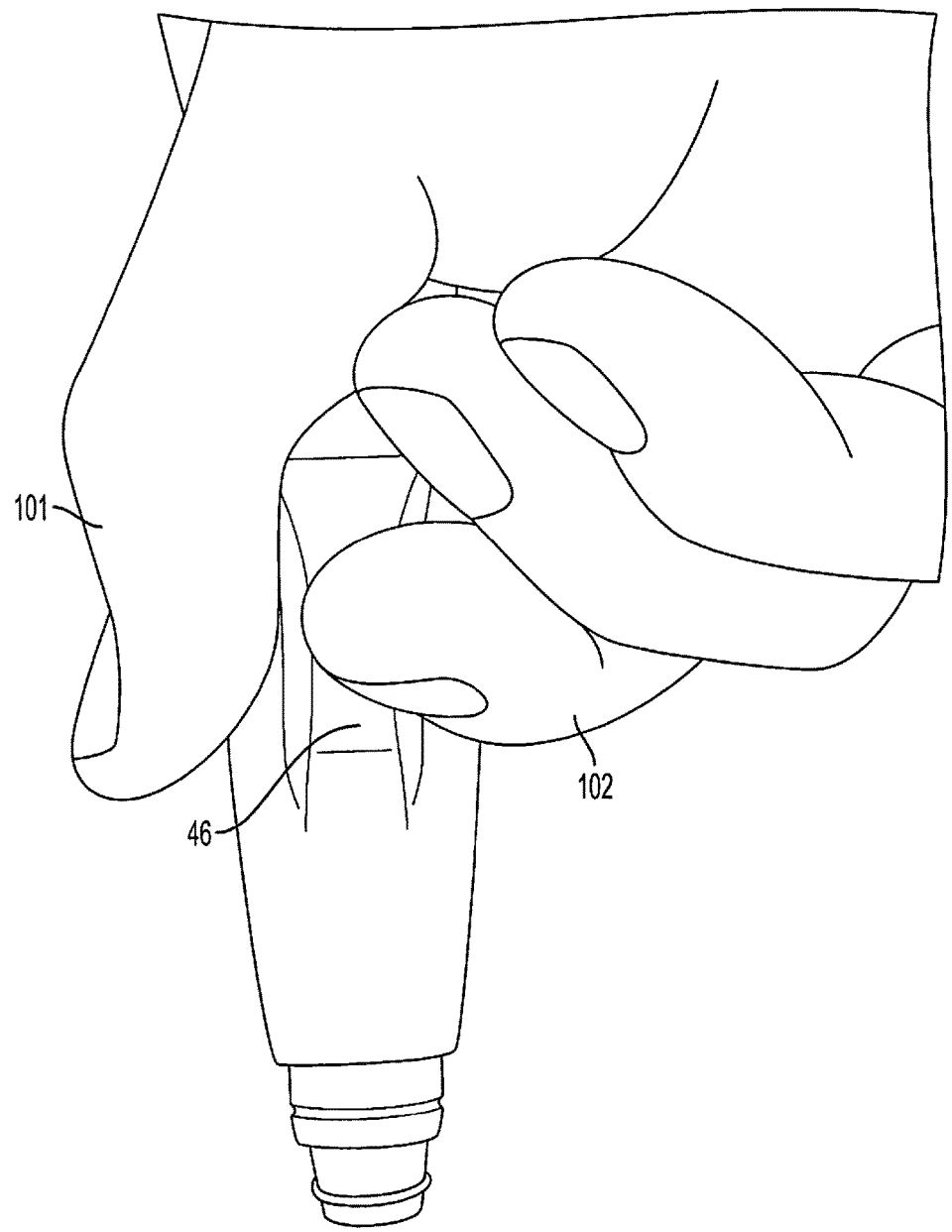
FIG. 14 is a rendition of the surgeon's hand holding the preferred embodiment of the present invention from a bottom view.

Referring now to FIGS. 14 and 15, the pencil-grip format is shown from a bottom view (FIG. 14) and a rear/top view at about a 45° angle (FIG. 15). Once again, the distal end of the index finger of the surgeon is used to press the forward button 58 or the rear button 60 for rotational movement of the drill motor.

Figure 18:
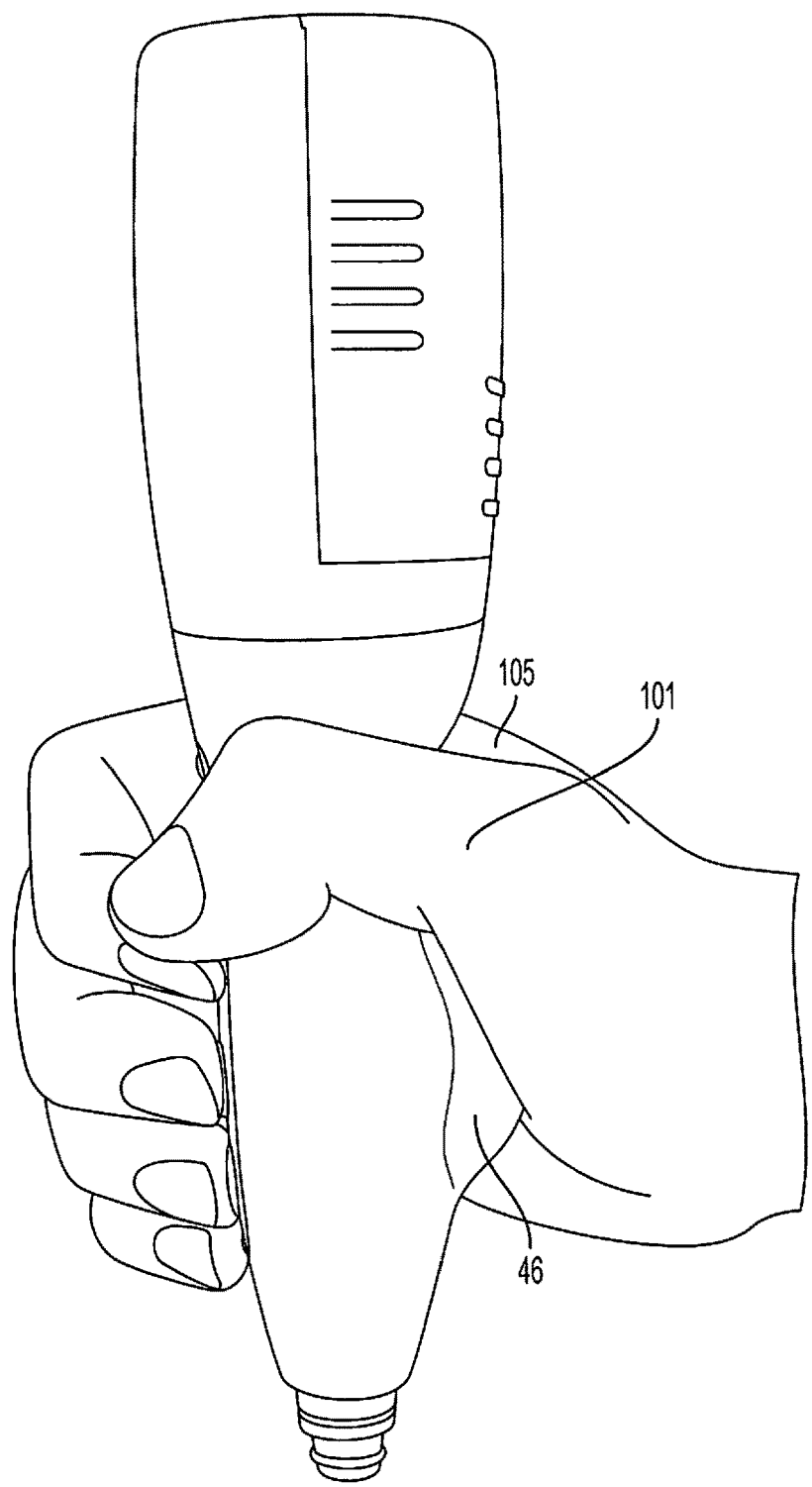
FIG. 18 is a rendition of the surgeon's hand gripping the preferred embodiment of the present invention with a bat-like grip, and the second, third, or fourth fingers operating the forward and reverse switches of the preferred embodiment of the present invention.

Referring now to FIGS. 16-18, various other hand grips of the present invention are shown that may be desirable, depending on the surgery being performed and the orientation of the surgeon relative to the target area. For example, the present invention permits the use of the thumb in a semi-grip format, as shown in FIG. 16. In this configuration, the unit is being held very similar to an electric eraser, permitting the surgeon to drill or screw in a direction substantially perpendicular to the target area with the thumb 101 operating the forward or reverse switches. The thumb 101 is operating the forward and reverse switches 58/60. In FIG. 17, a similar grip is shown, but with more of a batter's grip with all four fingers of the surgeon's hand being on the same side of the unit, but the thumb 101 still activating the forward or rear switches 58/60. Fin 46 provides a stop recess against which the index finger rests. Further, as shown in FIG. 18 the invention also provides a complete batter's grip with the second, third, or fourth fingers activating either/or the reverse or forward switches 58/60. With respect to this grip, fin 46 comfortably fits within the palm of the surgeon's hand, further stabilizing the unit, and region 56 comfortable fits within the V of the surgeon's hand between the base of the thumb 101 and the index finger 105.

In summary, various embodiments and examples of the present invention and associated methods have been disclosed. Although the disclosure has been in the context of those embodiments and examples, this disclosure extends beyond the specifically disclosed embodiments to other alternative embodiments and/or other uses of the embodiments, as well as certain modifications and equivalents thereof. Moreover, this disclosure expressly contemplates that various features and aspects of the disclosed embodiments can be combined with, or substituted for, one another. Accordingly, the scope of this disclosure should not be limited by the particularly disclosed embodiments described above, but should be determined only by a fair reading of the claims that follow.

What is claimed is:

1. A surgical tool comprising:
   a pencil-grip elongated housing having a proximal end and a distal end, said elongated housing having a tin member disposed proximate the distal end of the elongated housing positioned substantially coplanar with a longitudinal axis of the clang elongated housing;
   a removable battery source;
   a motor positioned in the elongated housing and configured to receive electrical power from the battery source; and
   a drive head positioned at the distal end of the tool, the drive head configured to be rotated by the motor so as to enable rotation of an attachment piece,
   wherein the elongated housing enables a surgeon to hold the distal end of the elongated housing in a pencil-grip manner with the fin stabilizing the housing during operation, and wherein one or more components of the surgical tool are disposed in the drive head such that a center of gravity of the tool is located proximal to the tin so that the center of gravity of the tool is configured to rest upon a "V" of a user's hand while the surgical tool is in use, the "V" comprising the area between a base of the user's thumb and a base of the user's index finger, wherein a shape of the distal end of the elongated housing includes a compound curve, with respect to the longitudinal axis, having a maximum curvature portion and a minimum curvature portion, the minimum curvature portion curving inwardly into the elongated housing toward the longitudinal axis and the maximum curvature portion curving outwardly away from the longitudinal axis, wherein an area of the tool that rests upon the "V" of the user's hand includes at least part of the minimum curvature portion of the compound curve, and wherein the fin is disposed at least in part within the maximum curvature portion of the compound curve.

2. The surgical tool according to claim 1, further comprising:
   a sensor that samples draw by the motor during operation of the motor; and
   a controller that receives a signal from the sensor indicative of the draw by the motor and uses such signals to determine a plurality of values with a torque applied to the bit that engages a screw when inserting the screw so as to provide torque-limiting capability.

3. The surgical tool according to claim 2, further comprising:
   a housing supporting a battery and removably connectable with said elongated housing, said battery housing having engaging means for attachment of said battery housing to the elongated housing and displaceable connector pins for engaging said controller to provide power.

4. The surgical tool according to claim 3, wherein said elongated housing includes interlocking rails and said battery housing includes complementary interlocking rails for slidable engagement with the interlocking rails of said elongated housing so as to engage and lock said battery housing to said elongated housing.

5. The surgical tool according to claim 3, wherein the battery is made of lithium.

6. The surgical tool according to claim 3, wherein the battery is disposable.

7. The surgical tool according to claim 3 wherein the battery is made of nickel cadmium.

8. The surgical tool according to claim 3, wherein the battery housing is configured to be disposed on the proximal end of the elongated housing.

9. The surgical tool according to claim 2, further comprising:
   a switch to disengage the controller, thereby permitting the operation of the surgical tool without torque-limiting capability.

10. The surgical tool according to claim 1 wherein the attachment piece is a bit to drive a screw, and wherein the tool is configured to stop rotation of the screw in response to a torque-limiting condition being satisfied.

11. The surgical tool according to claim 10, wherein the torque applied to the drive head is no more than about 30 inch-ounces.

12. The surgical tool according to claim 11, wherein the torque applied to the drive head is no more than about 20 inch-ounces.

13. The surgical tool according to claim 12, wherein the torque applied to the drive head is no more than about 10 inch-ounces.

14. The surgical tool according to claim 1, wherein the rotational speed of the drive head is reduced to less than or equal to 4,000 rpm.

15. The surgical tool according to claim 1, wherein the rotational speed of the drive head is reduced to less than or equal to 1,000 rpm.

16. The surgical tool according to claim 1, wherein the rotational speed of the drive head is no more than about 1,000 rpm.

17. A surgical tool comprising:
   a pencil-grip elongated housing having a proximal end and a distal end, said elongated housing having a fin disposed proximate the distal end of the elongated housing positioned substantially coplanar with a longitudinal axis of the elongated housing;
   a motor positioned in the elongated housing and configured to receive electrical power from a power source;
   a drive head positioned at the distal end of the tool, the drive head configured to receive either a drill bit or a bit configured to engage a screw, and to be rotated by the motor so as to enable rotation of the drill bit or the screw into a bone;

a sensor that monitors the motor during operation; and a controller that receives one or more signals from the sensor and uses such signals to determine a plurality of values with a torque applied to the bit that engages the screw when inserting the screw so as to provide torque-limiting capability, wherein the elongated housing enables a surgeon to hold the distal end of the elongated housing in a pencil-grip with the fin stabilizing the elongated housing during operation, and wherein the center of gravity of the tool is proximal the fin so that the center of gravity of the tool is configured to be generally proximal to a "V" of the surgeon's hand while the surgical tool is in use, the "V" comprising the area between the base of the surgeon's index finger and the base of the surgeon's thumb, wherein a shape of the distal end of the elongated housing includes a compound curve, with respect to the longitudinal axis, having a maximum curvature portion and a minimum curvature portion, the minimum curvature portion curving inwardly into the elongated housing toward the longitudinal axis and the maximum curvature portion curving outwardly away from the longitudinal axis, wherein an area of the tool that rests upon the "V" of the surgeon's hand include at least part of the minimum curvature portion of the compound curve, and wherein the fin is disposed at least in part within the maximum curvature portion of the compound curve.

18. The surgical tool according to claim 17, further comprising:
a power source having a battery housing removably connectable with said elongated housing, said battery housing having displaceable connector pins for engaging said controller.

19. The surgical tool according to claim 18, wherein the battery housing supports a battery to generate the electrical power, said battery in communication with said displaceable connector pins.

20. The surgical tool according to claim 19, wherein the battery is made of lithium.

21. The surgical tool according to claim 19, wherein the battery is disposable.

22. The surgical tool according to claim 19, wherein the battery is rechargeable.

23. The surgical tool according to claim 22, wherein the rechargeable battery is made of nickel cadmium.

24. The surgical tool according to claim 18, wherein the battery housing is configured to be disposed on the proximal end of the elongated housing.

25. The surgical tool according to claim 17, further comprising:
a switch to disengage the controller, thereby permitting the operation of the surgical tool without torque-limiting capability.

26. The surgical tool according to claim 17, wherein the drive head is configured to receive a bit that engages a screw, and wherein the tool is configured to stop rotation of the screw in response to a torque-limiting condition being satisfied.

27. The surgical tool according to claim 26, wherein the torque applied to the drive head is no more than about 30 inch-ounces.

28. The surgical tool according to claim 27, wherein the torque applied to the drive head is no more than about 20 inch-ounces.

29. The surgical tool according to claim 28, therein the torque applied to the drive head is no more than about 10 inch-ounces.

30. The surgical tool according to claim 17, wherein the rotational speed of the drive head is reduced to less than or equal to 4,000 rpm.

31. The surgical tool according to claim 17, wherein the rotational speed of the drive head is reduced to less than or equal to 1,000 rpm.

32. The surgical tool according to claim 17, wherein the rotational speed of the drive head is no more than about 1,000 rpm.

33. The surgical tool according to claim 17, further comprising:
a housing supporting a battery and removably connectable with said elongated housing, said battery housing having engaging means for attachment of said battery housing to the elongated housing and displaceable connector pins for engaging said controller to provide power.

34. The surgical tool according to claim 33, wherein said elongated housing includes interlocking rails and said battery housing includes complementary interlocking rails for slidable engagement with the interlocking rails of said elongated housing so as to engage and lock said battery housing to said elongated housing.

* * * * *

UNITED STATES PATENT AND TRADEMARK OFFICE
CERTIFICATE OF CORRECTION

PATENT NO. : 10,492,801 B2
APPLICATION NO. : 15/270875
DATED : December 3, 2019
INVENTOR(S) : Mario Gonzalez et al.

It is certified that error appears in the above-identified patent and that said Letters Patent is hereby corrected as shown below:

In the Claims

At Column 7, Claim number 1, Line number 27, delete "having a tin" and replace with --having a fin--.
At Column 7, Claim number 1, Line number 30, delete "axis of the clang elongated housing" and replace with --axis of the elongated housing--.
At Column 7, Claim number 1, starting at Line number 43, delete "proximal to the tin" and replace with --proximal to the fin--.
At Column 9, Claim number 17, Line number 24, delete "hand include" and replace with --hand includes--.
At Column 10, Claim number 29, Line number 20, delete "therein" and replace with --wherein--.

Signed and Sealed this
Third Day of March, 2020

Andrei Iancu
*Director of the United States Patent and Trademark Office*